United States Patent [19]

Vartanian

[11] 4,217,706
[45] Aug. 19, 1980

[54] BOOT FOR WALKING CAST

[76] Inventor: Vincent A. Vartanian, 11187 Jim Pl., Warren, Mich. 48089

[21] Appl. No.: 58,550

[22] Filed: Jul. 18, 1979

[51] Int. Cl.$^3$ ............................................. A43B 11/00
[52] U.S. Cl. ......................................... 36/110; 36/50
[58] Field of Search .................... 36/110, 105, 50, 7.1, 36/7.3, 4

[56] References Cited

U.S. PATENT DOCUMENTS

| Re. 6,522 | 6/1875 | Powell | 36/50 |
|---|---|---|---|
| 1,088,067 | 2/1914 | Forbes | 36/50 |
| 3,059,352 | 10/1962 | Clason | 36/50 |
| 3,905,135 | 9/1975 | Debusk | 36/110 |

Primary Examiner—Patrick D. Lawson
Attorney, Agent, or Firm—Robert G. Mentag

[57] ABSTRACT

A boot for a walking cast which includes a foot enclosure portion that is weathertight for the foot part of the cast, and which is integrally connected with an upwardly extended leg portion for covering the lower portion of the leg part of a walking cast. The foot enclosure portion is provided with an inner sole made from a resilient material such as foam rubber. The foot enclosure portion of the boot is provided with an outer top leather sole which is attached to a lower rubber sole that has a lower ground engaging serrated surface. The leg portion of the boot is provided with front and rear longitudinally extended zippers for dividing the leg portion of the boot into two parts which can be spread into an open position for quick and easy insertion of a walking cast into the boot. The two leg portion parts are each further provided with an expansion gusset for adjusting the snugness of the boot on the leg portion of the walking cast.

9 Claims, 4 Drawing Figures

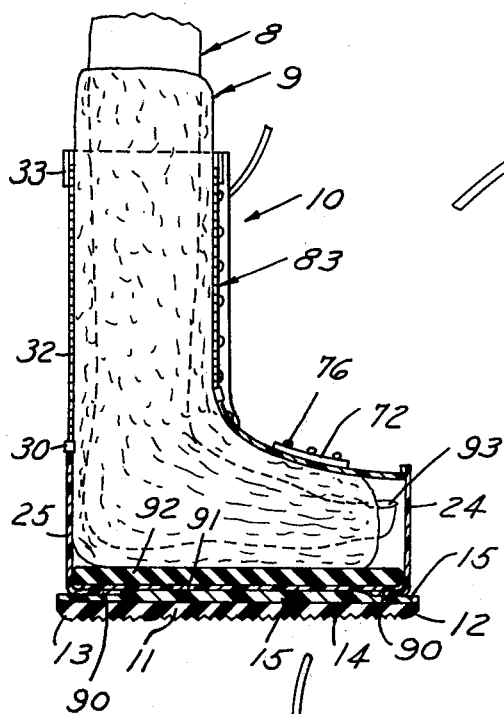
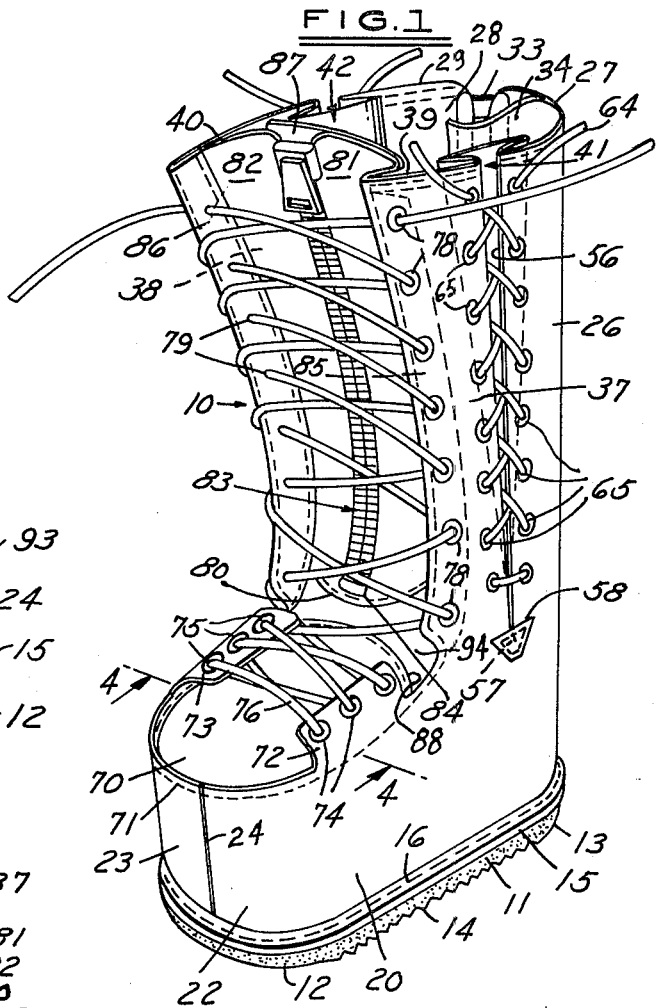
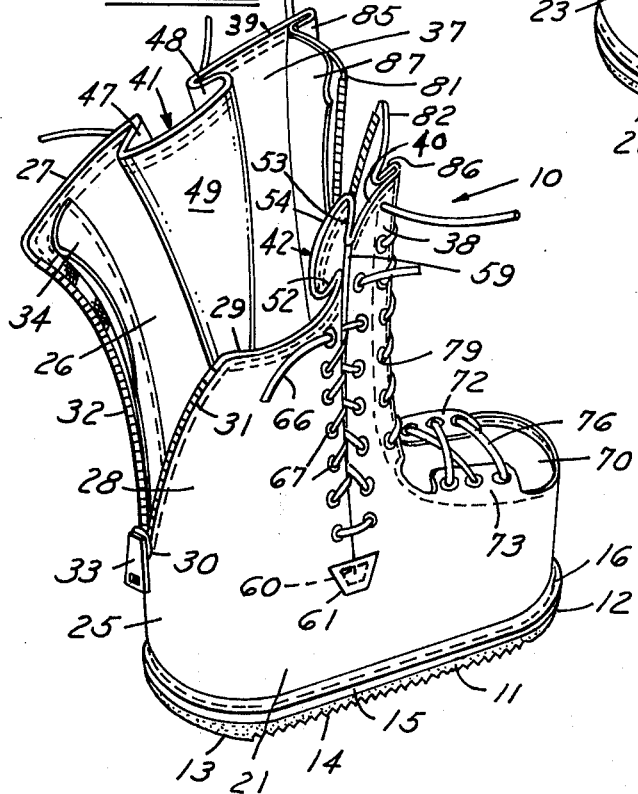
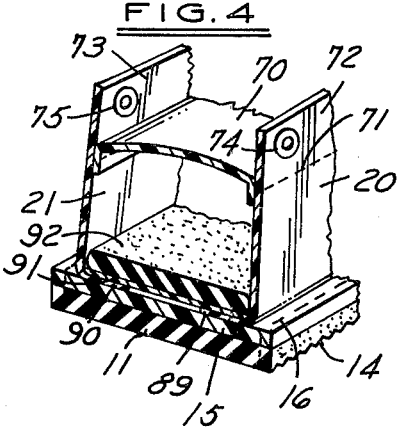

BOOT FOR WALKING CAST

BACKGROUND OF THE INVENTION

1. Field of the Invention

This invention relates to the boot art, and more particularly to a novel and improved boot for a walking case. The invention is specifically concerned with a walking cast which is constructed and arranged to allow the user to walk normally in all kinds of weather and protect the cast from rain, snow, and other weather elements.

2. Description of the Prior Art

It is well known in the boot art to provide boots of various constructions for mounting on a walking cast. Examples of such prior art walking cast boots are illustrated in U.S. Pat. Nos. 3,423,354; 2,598,217; 3,545,104; 3,566,487 and 3,905,135. U.S. Pat. No. 2,494,770 shows a boot wear having a closure zipper which extends for the length of the sole and up the back end thereof. U.S. Pat. No. 651,642 shows a shoe having expansion means on the bottom and sides thereof.

A disadvantage of some prior art walking cast boots is that they are not waterproof, and if they are waterproof, they do not provide any means for expansion on the sides and on the toe end thereof. A further disadvantage of some of the prior art walking cast boots is that they permit snow or rain to come in contact with the walking cast, and due to the construction of the cast, it disintegrates. A further disadvantage of some of the prior art walking cast boots is that they do not allow for any adjustments, so as to conform the shape of the boot to the shape of the walking cast to provide a snug fit.

SUMMARY OF THE INVENTION

In accordance with the present invention, a boot for a walking cast is provided which includes a foot enclosure portion that is weathertight to protect the foot part of a walking cast. The foot enclosure is integrally connected with an upwardly extended leg portion for covering the lower portion of the leg part of a walking cast. The upwardly extended leg portion is provided with front and rear longitudinally disposed zippers for dividing the leg portion of the boot into two parts which can be spread into an open position sidewardly for quick and easy insertion of a walking cast into the boot. The two leg portions that are each further provided with an adjustable expansion gusset means for further opening the side leg portions, and for adjusting the snugness of the boot on the leg portion of the walking cast after the walking cast has been inserted into the boot. The foot enclosure portion of the boot is provided with a lower rubber sole which has a lower ground engaging serrated surface and upwardly curved front and rear ends. The lower outer rubber sole is secured to an outer top leather sole which is in turn secured to the lower edges of the foot part of the boot.

The foot part or foot enclosure portion of the boot is provided with a lower inner leather sole and an upper inner resilient sole made from a suitable resilient material, such as foam rubber. The boot of the present invention permits a walking cast to be fully enclosed and protected against snow or rain, and other weather elements, to prevent deterioration of the walking cast. A person using the walking cast of the present invention can walk normally and carry out his working duties without any lost working time and resultant economic loss.

BRIEF DESCRIPTION OF THE DRAWINGS

FIG. 1 is a front elevational perspective view of a boot for a walking cast made in accordance with the principles of the present invention.

FIG. 2 is a central, elevation, longitudinal section view of the walking cast boot illustrated in FIG. 1.

FIG. 3 is a substantial, rear, elevation perspective view of the walking cast boot illustrated in FIG. 1, and showing each of the front and rear zippers in an open condition.

FIG. 4 is a fragmentary, elevational section view of the toe structure of the walking cast boot illustrated in FIG. 1, taken along the line 4—4 thereof, and looking in the direction of the arrows.

DESCRIPTION OF THE PREFERRED EMBODIMENT

Referring now to the drawing, and more particularly, to FIGS. 1, 2 and 3, the numeral 10 generally designates a walking cast boot made in accordance with the principles of the present invention. The numeral 8 generally designates the leg and foot of a person on which a conventional walking cast 9 is mounted over which the boot 10 is mounted. The numeral 11 designates an outer lower, ground engaging sole made from any suitable elastomeric material, such as rubber. In plane configuration, the outer lower sole 11 has straight, spaced apart edges, and curved front and rear ends. The plane configuration of the outer lower sole 11 would be substantially rectangular, with the corners rounded off. The ground engaging lower surface of the outer lower sole 11 is serrated, as indicated by the numeral 14, for optimum tractive engagement with the surfaces on which the user of the boot 10 would walk. The front and rear ends of the outer lower sole 11 are curved or tapered upwardly, as indicated by the numerals 12 and 13, respectively, from the front and rear termination points of the serrations 14, up to the front and rear sole ends, respectively, of the outer lower sole 11.

As shown in FIGS. 1 through 4, the boot 10 includes an outer top leather sole 15 which is fixedly secured to the top side of the lower outer sole 11 by any suitable means, as by a suitable adhesive, or by stitching as indicated by the numeral 16.

The boot 10 includes an integrally formed foot enclosure portion that is attached to the outer top leather sole 15 and which comprises a left side wall 20 and a right side wall 21. The boot enclosure portion is formed from any suitable material, as for example, leather. As shown in FIG. 1, the left and right sides 20 and 21, respectively, of the foot enclosure portion terminate in integrally rounded front end portions 22 and 23, respectively, which meet at a vertical joint line 24 where they are fixedly secured together by any suitable means, as by stitching. As shown in FIG. 3, the left and right parts of the foot enclosure portion are integrally connected to a rounded rear end portion 25.

The boot 10 includes an upwardly extended integral tubular leg portion which is divided into two arcuate side portions by a pair of longitudinally disposed zippers, as described hereinafter.

The left and right rear end members of the arcuate leg side portions comprise the upwardly extended leg parts 26 and 28 which are integrally joined at the lower ends with the foot portion of the boot, and which terminate at their upper ends marked by the numerals 27 and 29, respectively. As shown in FIG. 3, the adjacent rear edges of the leg parts 26 and 28 have each fixedly mounted thereon a conventional zipper strip, as 32, and 31, respectively. The numeral 30 indicates the lower end of the zipper strips 31 and 32. The zipper strips 31 and 32 are adapted to be interlocked, or parted into the open position, as by a conventional zipper slide member 33. A suitable longitudinal extended water seal flap 34, formed from the same material as the leg and foot portions of the boot, is attached along one side thereof to the inside of the leg portion 26 by any suitable means, as by stitching. The water seal flap 34 is adapted to overlap the zipper strips 31 and 32 when they are in the locked position, as shown in FIG. 1.

The left and right end members of the arcuate leg side portions comprise the upwardly extended leg parts 37 and 38 which are integrally joined at their lower ends with the foot portion of the boot, and which terminate at their upper ends, marked by the numerals 39 and 40, respectively. The left front side member 36 is spaced apart from the left rear end member 26 by an adjustable gusset generally indicated by the numeral 41. Similarly, the right front end member is spaced apart from the rear right end upward extended leg part 28 by an adjustable gusset generally indicated by the numeral 42.

As best seen in FIG. 3, the left adjustable gusset includes a rear triangular vertically disposed part 47 which is U-shaped, and has its outer end integral with the front end of the left leg portion 26. The gusset member 41 further includes a front triangular longitudinal part 48 which has its outer edge integral with the rear edge of the left side leg member 37. The inner edges of the triangular gusset member parts 47 and 48 are integrally formed with a central triangular, longitudinally disposed gusset member part 49. The gusset member 42 on the right side of the boot 10 is similarly formed with the rear and front triangular parts 62 and 53, respectively, and the integral central triangular part 54.

As shown in FIG. 1, when the outer edges of the gusset triangular parts 47 and 48 are adjacent each other, they meet along a vertical line 56, the lower end of which is indicated by the numeral 57. The lower end of the gusset meeting line 56 is enclosed by a suitable fixed seal tab 58 which seals the lower end of the gusset 41 against the weather. The seal tab 58 may be fixed to the boot side portions 26 and 37 by any suitable means, as by stitching. As shown in FIG. 3, the outer meeting line of the gusset parts 52 and 53 of the gusset 42 is indicated by the numeral 59, and the lower end thereof is indicated by the numeral 60. The lower end of the gusset meeting line 59 is enclosed by a suitable fixed seal tab 61 which is secured by any suitable means as by stitching to the boot side portions 28 and 38.

As shown in FIG. 1, the expandable gusset 41 is provided with means for pulling gusset parts 47 and 48 together along the parting line 56, and it comprises a suitable boot lacing 64 which is operatively mounted through a plurality of lacing eyelets 65 that are formed through the leg side portions 26 and 37 adjacent the meeting line 56. As shown in FIG. 3, the adjustable gusset 42 is provided with a similar lacing 66 that is operatively mounted through suitable lacing eyelets 67 that are operatively mounted in the right side parts 28 and 38.

As shown in FIG. 1, the boot 10 includes a toe cover part 70 which is made from the same material as the foot and leg portions of the boot, and it is disposed over the toe portion of the walking cast 9. The toe cover part 70 is shaped with a curved front end and it is attached to the foot side protions 21, 22 and 23 by any suitable means as by suitable stitching 71 (FIG. 4.). An integral boot lace flap 72 is formed along the upper edge of the foot side portion 20 and a similar boot lace flap 73 is formed along the upper edge of the foot portion 21. The boot lace flaps 72 and 73 are provided with suitable lacing eyelets 74 and 75, respectively, through which is operatively mounted the lower end of a suitable boot lacing 76. The leg side portions 37 and 38 are provided with suitable spaced lacing eyelets 78 and 79 along their front edges for the reception of the upper portion of the boot lacing 76.

The vertical space between the front lower edges of the leg portion front members 37 and 38 is enclosed by a pair of vertical disposed, left and right front covers strips 81 and 82, respectively, which have their vertical outer edges secured to the side portions 37 and 38 by any suitable means, as by stitching.

As shown in FIG. 1, the front cover strips 81 and 82 have their inner edges operatively connected to the zipper strip parts of a suitable zipper 83 for opening and closing the front cover strips 81 and 82. The lower end of the front strips 81 and 82 is indicated by the numeral 80 in FIG. 1. The space between the lower edge 80 of the front cover strips 81 and 82, and the rear edge 88 of the toe cover part 70 is enclosed by a suitable connector strip 94 which is secured by any suitable means, as by stitching, to the strips 81 or 82, and the toe cover 70. The lower end of the zipper 83 is indicated by the numeral 84.

As shown in FIGS. 1 and 3, the front leg parts 37 and 38 have a folded-over edge 85 and 86, respectively, which overlaps the outer edges of the front cover strips 81 and 82, respectively. A vertically disposed water seal flap 87 is mounted behind the zippers 83, with the one longitudinal edge being operatively fixed to the left leg member 37 by means of the folded-over edge 85 and suitable stitching. 20 is folded inwardly and under a lower inner sole 91 made from a suitable material, as from leather. The lower edge 90 of the right side 21 of the foot portion of the boot 10 is also folded inwardly under the lower inner sole 91. A suitable upper inner sole 92 is mounted over the inner leather sole 91, and it is made from any suitable resilient material, such as, 3/4 inch foam rubber, or the like. The inner soles 91 and 92 may be secured in place by any suitable means, as by a suitable adhesive, or by stitching.

The numeral 93 in FIG. 2 shows the toe of the leg of the user of the boot 10 being enclosed within the boot and protected from the weather.

In use, the front zipper 83 is opened, and the rear zipper slide. member 33 is moved downward to also open the rear zipper. The adjustable gussets 41 and 42 are released and moved to an open position, and the front lace 76 is loosened. It will thus be seen that the side portions of the boot 10 can than be spread open so that the walking cast 9 can be quickly and easily be inserted into the boot 10. The front and rear zippers, and the adjustable gussets are then closed to a snug position around walking cast 9. The front lace 76 is also then snuggd up to a desired adjusted position.

It will be seen that the boot 10 of the present invention provides a covering member for a walking cast which permits the cast to be made without the need for any metal ground engaging member. The boot of the present invention is also waterproof and protects the walking cast 9 from any breakdown due to water, snow and other weather elements. The foam rubber inner sole 92 permits the user to walk with total freedom from restrictions which would otherwise be present with the use of crutches. The user of the boot 10 can walk normally and go about his work without losing work time. The boot 10 of the present invention also insures proper healing of a broken bone since the walking cast is fully protected and will not break when the boot 10 is worn during normal walking.

It will be understood that the upper outer sole 15 may also be made from a suitable rubber, or the like material, and that the foot and leg portions of the boot may be made from any suitable material such as leather, plastic, and the like. The boot 10 is shaped to fit either the left or right foot of a user.

While it will be apparent that the preferred embodiment of the invention herein disclosed is well calculated to achieve the results aforestated, it will be appreciated that the invention is susceptible to modification, variation and change.

What I claim is:

1. In a weatherproof boot for a surgical walking cast having leg and foot portions, the combination comprising:
   (a) an enclosed foot portion having an outer sole means;
   (b) a leg portion attached to the foot portion and including a pair of side parts;
   (c) each of said side parts having an intermediate adjustable gusset means;
   (d) means for connecting together and disconnecting the rear ends of the leg portions for closing and opening, respectively, the rear end of the boot leg portion; and,
   (e) means for connecting together and disconnecting the leg portions at their front ends for closing and opening, respectively, the front end of the boot leg portion.

2. A boot for a surgical walking cast as defined in claim 1, wherein:
   (a) said means for connecting together and disconnecting the leg portion side parts at their front and rear ends comprises a zipper means.

3. A boot for a surgical walking cast as defined in claim 2, wherein:
   (a) said means for connecting together the leg side parts at their front ends includes a pair of cover strips which are opened and closed by said zipper means.

4. A boot for a surgical walking cast as defined in claim 2, including a water seal tab attached to one of the leg portion side parts adjacent each zipper means, and extended over the length of each zipper means on the inner side thereof.

5. A boot for a surgical walking cast as defined in claim 4, wherein:
   (a) each of said gusset means includes a lacing for snugging each leg portion side part in place against the walking cast.

6. A boot for a surgical walking cast as defined in claim 5, including:
   (a) a lacing operatively mounted along the front ends of the pair of leg portion side parts for snugging the boot in place on the walking cast.

7. A boot for a surgical walking cast as defined in claim 6, wherein:
   (a) the outer sole means includes a ground engaging sole having a serrated lower surface.

8. A boot for a surgical walking cast as defined in claim 7, including:
   (a) an inner resilient cushion sole.

9. A boot for a surgical walking cast as defined in claim 8, wherein:
   (a) the lower surface of the ground engaging sole is curved upwardly at the front and rear ends of said sole.

* * * * *

UNITED STATES PATENT OFFICE
CERTIFICATE OF CORRECTION

Patent No. 4,217,706   Dated   August 19, 1980

Inventor(s)   VINCENT A. VARTANIAN

It is certified that error appears in the above-identified patent and that said Letters Patent are hereby corrected as shown below:

Column 4, line 40, after "stitching", begin new paragraph.

Column 4, line 40, before "20", insert --As shown in Figure 4, the lower edge 89 of the left side foot portion--.

Column 4, line 58, delete "than" and insert --then--.

Signed and Sealed this

Eighteenth Day of November 1980

[SEAL]

Attest:

SIDNEY A. DIAMOND

Attesting Officer   Commissioner of Patents and Trademarks